(12) United States Patent
Elbogen et al.

(10) Patent No.: US 10,016,360 B1
(45) Date of Patent: *Jul. 10, 2018

(54) COMPOSITIONS, USES AND METHODS FOR MAKING THEM

(71) Applicants: Steven Elbogen, San Diego, CA (US); Don Wirtshafter, San Diego, CA (US)

(72) Inventors: Steven Elbogen, San Diego, CA (US); Don Wirtshafter, San Diego, CA (US)

(*) Notice: Subject to any disclaimer, the term of this patent is extended or adjusted under 35 U.S.C. 154(b) by 881 days.

This patent is subject to a terminal disclaimer.

(21) Appl. No.: 14/444,111

(22) Filed: Jul. 28, 2014

Related U.S. Application Data

(60) Provisional application No. 61/859,102, filed on Jul. 26, 2013.

(51) Int. Cl.

| | |
|---|---|
| *A61K 36/185* | (2006.01) |
| *A61K 9/00* | (2006.01) |
| *A61K 36/28* | (2006.01) |
| *A61K 36/53* | (2006.01) |
| *A61K 36/73* | (2006.01) |
| *A61K 36/77* | (2006.01) |
| *A61K 36/84* | (2006.01) |
| *A61K 36/67* | (2006.01) |
| *A61K 36/296* | (2006.01) |
| *A61K 47/10* | (2017.01) |
| *A61K 45/06* | (2006.01) |

(52) U.S. Cl.
CPC ............ *A61K 9/007* (2013.01); *A61K 36/185* (2013.01); *A61K 36/28* (2013.01); *A61K 36/296* (2013.01); *A61K 36/53* (2013.01); *A61K 36/67* (2013.01); *A61K 36/73* (2013.01); *A61K 36/77* (2013.01); *A61K 36/84* (2013.01); *A61K 45/06* (2013.01); *A61K 47/10* (2013.01)

(58) Field of Classification Search
CPC .................................................... A61K 36/185
USPC .......................................................... 424/774
See application file for complete search history.

(56) References Cited

U.S. PATENT DOCUMENTS

2008/0139667 A1* 6/2008 Robson ................ A61K 31/047
514/733

* cited by examiner

Primary Examiner — Christopher R Tate
Assistant Examiner — Deborah A Davis
(74) Attorney, Agent, or Firm — Dinsmore & Shohl LLP; Aubrey A. Haddach

(57) ABSTRACT

Disclosed are compositions containing chemical constituents from plants, uses of these compositions and methods for making them. In various embodiments, the present invention relates to an improved modes of administration of herbal remedies.

7 Claims, No Drawings

COMPOSITIONS, USES AND METHODS FOR MAKING THEM

RELATED APPLICATIONS

This application claims the benefit of the priority of U.S. Provisional Application No. 61/859,102, filed Jul. 26, 2013, which is incorporated herein by reference in its entirety.

FIELD OF THE INVENTION

Generally, the present invention relates to compositions containing chemical constituents from plants, uses of these compositions and methods for making them. In various embodiments, the present invention relates to an improved mode of administration for *cannabis* and its natural and synthetic derivatives. The term *cannabis* is used herein to refer to all physiologically active substances derived from the *cannabis* family of plants and synthetic *cannabis* analogues and derivatives, precursors, metabolites or related substances having *cannabis*-like physiological effects. Non-limiting examples of *cannabis* include *Satvia, Indica* and *Ruderalis*.

BACKGROUND OF THE INVENTION

Herbal extracts and formulations have long been used and/or suggested for well-being in humans. Efficacy varies for such extracts and formulations. Generally, such treatments are either topical or systemic, but sometimes can be both. In the art, the term "well-being" is used to refer to a person's general health, particularly physical health, and well-being. In more recent times the term "wellness" has been coined, though no particular connotation boundaries are strictly applied to any of these terms. In this specification, the term "well-being" is used in an encompassing sense to embrace such concepts including those described above unless the context requires otherwise.

The medicinal and psychoactive properties of the *cannabis* plant have been known for centuries. Evidence suggests that *cannabis* is a safe, versatile and potentially inexpensive drug. It has been reported as being beneficial to patients suffering from a wide range of symptoms experienced in connection with various, often very serious, medical conditions. For example, *cannabis* has been used to alleviate symptoms associated with cancer, anorexia, AIDS, chronic pain, glaucoma, arthritis, migraine and many other illnesses. *Cannabis* is recognized as having anti-emetic properties and has been successfully used to treat nausea and vomiting in cancer patients undergoing chemotherapy. Studies also report use of *cannabis* in treating the weight loss syndrome of AIDS and in reducing intraocular pressure for the treatment of glaucoma. *Cannabis* is also reported to have muscle relaxing effects.

Currently, the main method of administering *cannabis* to a patient in need is lung delivery, typically achieved by smoking *cannabis*. Unfortunately, there are concerns about the effect of this mode of administration on the lungs. *Cannabis* smoke carries even more tars and other particulate matter than tobacco, and so may be a cause of lung cancer. It is known that some of the chemicals produced by smoking *cannabis* are aggressive and smoking has been shown to cause the gradual dissolving of teeth.

Attempts have been made to overcome some of the problems associated with smoking both *cannabis* and tobacco by providing various smokeless inhalable aerosol formulations for lung delivery. A self-propelled inhalable aerosol of delta-9-tetrahydrocannabinol was developed as long ago as 1975 as a bronchodilator. Inhalable aerosol formulations were made comprising either only liquid components and or including a solid particulate component carrying the active agent, such as the *cannabis*. The various formulations were found to be of varying effectiveness in delivering the active agent to the alveoli of the lungs in the same manner as smoke.

However, both methods of lung delivery discussed above have been found to cause a pronounced and involuntary cough, possibly from irritation of the trachea and lungs. This unpleasant side effect is not overcome by the smoke-free method of lung delivery.

The present invention aims to provide formulations and treatments for well-being in humans which alleviate one or more of the shortcomings of the prior art. Other aims and advantages of the invention may become apparent from the following description.

SUMMARY OF THE INVENTION

In various embodiments, provided herein is a vaporization delivery method and compositions to use in vaporization delivery.

In some embodiments, the vaporization delivery method consists essentially of administering an herbal medicine in a carrier comprising a glycol wherein the herbal medicine is delivered to the patient through vaporization of the glycol. In other embodiments, the vaporization delivery method consists essentially of administering an herbal medicine in a carrier comprising vegetable glycerin wherein the herbal medicine is delivered to the patient through vaporization of the vegetable glycerin.

In various embodiments, the delivery method further comprises an extraction step. In these embodiments, the extraction step is performed by adding the plant material to the glycol to create a first composite, storing the first composite at a temperature between about −34° C. to about −18° C. for at least about 4 hours, grinding the first composite for about 5 to about 15 minutes to create a second composite, storing the second composite at a temperature between about −34° C. to about −18° C. for at least about 4 hours, grinding the second composite for about 5 to about 15 minutes to create a third composite and removing the unwanted material from the third composite.

In specific embodiments, the first composite is stored at the lower temperature for between about 2-24 hours, or about 4-8 hours, or about 4-12 hours, or about 4-16 hours, or about 4-24 hours, or about 8-12 hours, or about 8-24 hours. In some embodiments, the first composite is stored at the lower temperature for between about 2 hours, or about 4 hours, or about 6 hours, or about 8 hours, or about 10 hours, or about 12 hours, or about 14 hours, or about 16 hours, or about 20 hours, or about 22 hours, or about 24 hours.

In various specific embodiments, the first composite is ground for between about 2-60 minutes, or about 5-45 minutes, or about 5-30 minutes, or about 10-15 minutes. In some embodiments the first composite is ground for about 5 minutes, or about 10 minutes, or about 15 minutes, or about 20 minutes, or about 25 minutes, or about 30 minutes, or about 35 minutes, or about 40 minutes, or about 45 minutes.

In specific embodiments, the second composite is stored at the lower temperature for between about 2-24 hours, or about 4-8 hours, or about 4-12 hours, or about 4-16 hours, or about 4-24 hours, or about 8-12 hours, or about 8-24 hours. In some embodiments, the second composite is stored at the lower temperature for between about 2 hours, or about 4 hours, or about 6 hours, or about 8 hours, or about 10 hours, or about 12 hours, or about 14 hours, or about 16 hours, or about 20 hours, or about 22 hours, or about 24 hours.

In various specific embodiments, the second composite is ground for between about 2-60 minutes, or about 5-45 minutes, or about 5-30 minutes, or about 10-15 minutes. In some embodiments the second composite is ground for about 5 minutes, or about 10 minutes, or about 15 minutes, or about 20 minutes, or about 25 minutes, or about 30 minutes, or about 35 minutes, or about 40 minutes, or about 45 minutes.

In some specific embodiments, the herbal medicine is an antiseptic, emollient, astringent, diuretic, bitter, carminative, cholagogues, choleretic, demulcent, hepatics, laxative, stomachic, analgesics, anti-inflammatory, antispasmodics, relaxants, sedative, stimulant, cardiotonic, circulatory stimulant, diaphoretic, spasmolytic, depurative, healer, immune stimulant, antiseptic, antibiotic, espectorant, demulcent, adaptogen, hormonally active herb, or emmenagogue.

In various specific embodiments, the antiseptic is *melaleuca alternifolia*; the emollient is *officinalis*; the astringent is *hamamelis virginiana, equisetum arvense, polygonum bistorta*, or a combination thereof; the diuretic is *zea mays*; the bitter is *Artemisia absinthum*; the carminative is *acorns calamus*; the cholagogue is *chinanthus virginicus*; the choleretic is *cynara scolymus*; the demulcent is *plantago* sppl; the hepatic is *bupleurum* Chinese; the laxative is *cassia senna*; the stomachic is *eletteria cardamomum*; the analgesic is *gelsemium sempervirens*; the anti-inflammatory is *salix alba*; the antispasmodic is *cinchona*; the nervine is *rosmarinus officinalis*; the relaxant is *melissa officinalis, cannabis*, or a mixture thereof; the sedative is *viscum album*; the stimulant is *cola acuminate*; the tonic is *avena sativa*; the cardiotonic is *salvia miltiorrhiza*; the circulatory stimulant is *capsicum frutescens*; the diaphoretic is *chrysanthemum× morifolium*; the spasmolytic is *viurnum opulus; cannabis; ammi visnaga*, or a mixture thereof; the depurative is *arctium lappa*; the healer is *prunella vulgaris, symphytum officinale* or a mixture thereof; the immune stimulant is *echinacea* spp., *tabebuia* spp. or a mixture thereof; the antiseptic and/or antibiotic is *allium sativum barosma betulina, zingiber officinale*, or a combination thereof; the espectorant is *inula helenium*; the demulcent is *althaea officinalis*; the adaptogen is *panax ginseng*; the hormonally active herb is *vitex agnus-castus*; and the emmenagogue is *cimicifuga racemosa*.

In some embodiments, the herbal medicine comprises one or more constituents selected from Milk Thisle Seed, Holy Basil, Meadowsweet, Guarana, Yerba Mate, Valerian, Hops, Kava Kava, Damiana, Catuaba Bark, and Horny Goat Weed. In other embodiments, the herbal medicine comprises cannabidiol. In still other embodiments, the herbal medicine comprises *cannabis*.

Other features and advantages of the present disclosure will become more readily apparent to those of skill in the art after reviewing the following detailed description and accompanying drawings.

DETAILED DESCRIPTION OF ILLUSTRATIVE EMBODIMENTS

After reading this description it will become apparent to one skilled in the art how to implement the compositions and methods of the present disclosure in various alternative embodiments and alternative applications. However, although various embodiments of the present disclosure will be described herein, it is understood that these embodiments are presented by way of example only, and not limiting. As such, this detailed description of various alternative embodiments should not be construed to limit the scope or breadth of the present disclosure as set forth in the appended claims.

Exemplary Terms

As used herein, the terms "comprising," "including," and "such as" are used in their open, non-limiting sense.

The term "about" is used synonymously with the term "approximately." Illustratively, the use of the term "about" indicates that values slightly outside the cited values, i.e., plus or minus 0.1% to 10%, which are also effective and safe.

"Antioxidants" include, e.g., butylated hydroxytoluene (BHT), butylated hydroxyanisole (BHA), sodium ascorbate, and tocopherol.

"Binders" impart cohesive qualities and include, e.g., alginic acid and salts thereof; cellulose derivatives such as carboxymethylcellulose, methylcellulose (e.g., Methocel), hydroxypropylmethylcellulose, hydroxyethylcellulose, hydroxypropylcellulose (e.g., Klucel), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone®, CL, Kollidon® CL, Polyplasdone® XL-10), larch arabogalactan, Veegum®, polyethylene glycol, waxes, sodium alginate, and the like.

"Pharmaceutically-acceptable excipients" include any commonly used materials in pharmaceutics and should be selected on the basis of compatibility with the active ingredient and the release profile properties of the desired dosage form. Exemplary pharmaceutically-acceptable excipients include, e.g., carriers, binders, suspending agents, disintegration agents, filling agents, surfactants, solubilizers, stabilizers, lubricants, wetting agents, diluents, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott William & Wilkins 1999).

"Prevent" or "prevention" means no disorder or disease development if none had occurred, or no further disorder or disease development if there had already been development. Also considered is the ability of one to prevent or reduce some or all of the symptoms associated with the disorder or disease.

"Surfactants" include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF); and the like.

A "therapeutically effective amount" or "effective amount" is that amount of a compound, material, composition, and/or dosage form as described herein that is in at least some cases effective to achieve a particular biological result.

Such effective activity is achieved in at least some cases, for example, by causing the ingestion of compositions according to aspects of the present disclosure. The term "therapeutically effective amount" includes, for example, a prophylactically effective amount. An "effective amount" is an amount effective to achieve a desired pharmacologic effect or therapeutic improvement without undue adverse side effects. The effective amount of a pharmaceutical agent will be selected by those skilled in the art depending on the particular patient and the disease level. It is understood that "an effective amount" or "a therapeutically effective amount" varies in at least some cases from subject to subject, due to variation in metabolism of therapeutic agents, age, weight, general condition of the subject, the condition being treated, the severity of the condition being treated, and the judgment of the prescribing physician.

"Treat" or "treatment" includes preventing a disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression (or partial regression) of the disorder or disease, relieving a condition caused by the disease or disorder, stopping the symptoms of the disease or disorder, or reversing or partially reversing certain diseases and/or conditions. Thus, as used herein, the term "treat" is used synonymously with the term "prevent."

The invention described herein resides broadly for well-being in humans through the use of extracts from plants. In specific embodiments, provided herein is a novel process that provides a more complete extraction of herbal medicines from plants.

Various other embodiments of the invention relate to an improved mode of administration (e.g., vaporization with an electronic cigarette) for herbal remedies, such as *cannabis* and its natural and synthetic derivatives. Pharmaceutical compositions suitable for vaporization of these herbal remedies and novel method for extracting herbal remedies from their sources are provided herein.

The term *cannabis* is used herein to refer to all physiologically active substances derived from the *cannabis* family of plants and synthetic *cannabis* analogues and derivatives, precursors, metabolites, or related substances having *cannabis*-like physiological effects. Non-limiting specific examples of *cannabis* variants include *Sativa*, *Indica* and *Ruderalis*.

In various embodiments, cannabidiol (CBD) is included in the herbal medicine. The term cannabidiol includes any non-psychotropic phytocannabinoid. Non-limiting specific examples of CBD strains are Sour Tsunami, Harlequin, Omrita Rx3, Jamaican Lion, Cannatonic, Juanita la Lagrimosa, Misty, Good Medicine, Maz's Cheese, TBxOGK, OG Afghani, Jamaican Skunk, Atomic Jam, Downtown Diesel, Cotton Candy×Diesel, and Sugaree×Blue Diesel.

Specific non-limiting examples of other specific herbal medicines useful in various embodiments of the invention described herein include:
  a. Antiseptics such as *melaleuca alternifolia*;
  b. Emollients such as *calendula officinalis*;
  c. Astringents such as *hamamelis virginiana, equisetum arvense, polygonum bistorta*;
  d. Diuretics such as *zea mays*;
  e. Bitters such as *Artemisia absinthum*;
  f. Carminatives such as *acorns calamus*;
  g. Cholagogues such as *chinanthus virginicus*;
  h. Choleretics such as *cynara scolymus*;
  i. Demulcents such as *plantago* sppl;
  j. Hepatics such as *bupleurum* Chinese;
  k. Laxatives such as *cassia senna*;
  l. Stomachics such as *eletteria cardamomum*;
  m. Analgesics such as *gelsemium sempervirens*;
  n. Anti-inflammatories such as *salix alba*;
  o. Antispasmodics such as *cinchona*;
  p. Nervines such as *rosmarinus officinalis*;
  q. Relaxants such as *melissa officinalis* and *cannabis*;
  r. Sedatives such as *viscum album*;
  s. Stimulants such as *cola acuminate*;
  t. Tonics such as *avena sativa*;
  u. Cardiotonics such as *salvia miltiorrhiza*;
  v. Circulatory stimulants such as *capsicum frutescens*;
  w. Diaphoretics such as *chrysanthemum×morifolium*;
  x. Spasmolytics such as *viurnum opulus; cannabis*; and *ammi visnaga*;
  y. Depuratives such as *arctium lappa*;
  z. Healers such as *prunella vulgaris* and *symphytum officinale*;
  aa. Immune Stimulants such as *echinacea* spp. and *tabebuia* spp.;
  bb. Antiseptics and Antibiotics such as *allium sativum barosma betulina, zingiber officinale*;
  cc. Espectorants such as *inula helenium*;
  dd. Demulcents such as *althaea officinalis*;
  ee. Adaptogens, such as *panax ginseng*;
  ff. Hormonally active herbs such as *vitex agnus-castus*; and
  gg. Emmenagogues such as cimicifuga *racemosa*.

Phenols include a wide-ranging group of plant constituents from salicylic acid to complex sugar-containing phenolic glycosides. These constituents are often anti-inflammatory and antiseptic. In some embodiments, the plant is a phenol such as *rosmarinic* acid, *gaultheria procumbens, salix alba* and *thymus vulgaris*.

In various embodiments the plant constituent is a volatile oil. Non-limiting examples of volatile oils useful in the present invention are *melaleuca alternifolioa, myrica gale, Chamomilla recutita*, and *pinus sylvestris*.

Flavanoid constituents are also useful in various embodiments of the present invention. Non-limiting examples of flavonoids are *fagopyrum esculentum, citrus* lemon, and *trifolium* pretense.

In various embodiments, the constituent is tannin or proanthocyanin. Non limiting examples of tannins include *quercus robur* and acacia *catechu*. Non-limiting examples of proanthocyanins are *robus fruticosus, vitis vinifera* and *crataegus oxycantha*.

Coumarin constituents are also useful various embodiments of the invention. Non-limiting examples of coumarins include *melilotus officinalis, aesculus hippocastanum, apium graveolens* and *ammi visnaga*.

In some embodiments, the constituent is a saponin and/or anthraquinone. Non-limiting examples of coumarins are melilotus *officinalis, aesculuc hippocastanum, apium graveolens*, and *ammi visnaga*. Non-limiting examples of saponins are *dioscorea villosa, glycyrrhiza glabra* and *primula veris*.

Cardia Glycosides and Cyanogenic Glycosides are other constituents useful in the present invention in various embodiments. Non-limiting examples of cardia glycosides are *prunus serotina, sambucas nigra* and *prunus armeniaca*. Non-limiting examples of cardiac glycosides are *digitalis purpurea* and *convallaria majalis*.

Polysaccharides, including but not limited to *ulmus rubra, linum usitatissimum* and aloe vera; Glucosilinates such as

*raphanus sativus* and *nasturtium officinale*, and Bitters including but not limited to *Artemisia absinthium, swertia chirata* and *humulus lupulus*, are other constituents useful in various embodiments of the present invention.

In further embodiments, alkaloids such as *vinca rosea* and *atropa belladonna*; vitamins such as *citrus limon, daucus carota, nasturtium officinale*, and *hippophae rhamnoides*; and minerals such as *brassica oleracea, fucas vesiculosis, taraxacum officinale* and *equisetum arvense*; are other non-limiting examples of constituents useful in the present invention.

The above description of the disclosed embodiments is provided to enable any person skilled in the art to make or use the methods and compositions of the present disclosure. Various modifications to these embodiments will be readily apparent to those skilled in the art, and the generic principles described herein can be applied to other embodiments without departing from the spirit or scope of the disclosure. Thus, it is to be understood that the description and drawings presented herein represent a presently preferred embodiment of the disclosure and are therefore representative of the subject matter which is broadly contemplated by the present disclosure. It is further understood that the scope of the present disclosure fully encompasses other embodiments that may become obvious to those skilled in the art and that the scope of the present disclosure is accordingly not limited.

EXAMPLES

Example 1: Room Temperature Extraction of Medicinal Constituent from Plant

Add a glycol, such as propylene glycol (12 mL), to plant material, such as *cannabis* (2 grams), to create a first composite and mix the first composite at room temperature for 24 hours. Mash the first composite for 15 minutes to create a second composite. Pour the second composite through nylon, or other suitable mesh, to remove the unwanted material and finalize a homogeneous solution with the constituent(s) desired. Load the homogeneous solution into a cartomizer for use in combination with an electronic cigarette.

Example 2: Hot Extraction of Medicinal Constituent from Plant

Add a glycol, such as propylene glycol (12 mL), to plant material, such as *cannabis* (2 grams), to create a first composite and mix the first composite in a closed loop system at a temperature between 110° C. to 150° C. for 12 hours. Mash the first composite for 15 minutes to create a second composite. Heat the second composite in a closed loop system at a temperature between 110° C. to 150° C. for 12 hour. Mash the second composite for 15 minutes to create a third composite. Pour the third composite through nylon, or other suitable mesh, to remove the unwanted material and finalize a homogeneous solution with the constituent(s) desired. Load the homogeneous solution into a cartomizer for use in combination with an electronic cigarette.

Example 3: Cold Extraction of Medicinal Constituent from Plant

Add a glycol, such as propylene glycol (12 mL), to plant material, such as *cannabis* (2 grams), to create a first composite and store the first composite in a cold room at a temperature between −34° C. to −18° C. for 8 hours. Remove the first composite from the cold room and mash it up for 15 minutes to create a second composite, put the second composite into the cold room for 8 hours. Remove the second composite from the cold room and mash it up for 15 minutes to create a third composite. Pour the third composite through nylon, or other suitable mesh, to remove the unwanted material and finalize a homogeneous solution with the constituent(s) desired. Load the homogeneous solution into a cartomizer for use in combination with an electronic cigarette.

| Indication | Constituents |
| --- | --- |
| Hangover Remedy Formula | Milk Thisle Seed, Holy Basil, Meadowsweet |
| Energy Formula | Guarana, Yerba Mate |
| Relaxation Formula | Valerian, Hops, Kava Kava |
| Sexual Enhancement Formula | Damiana, Catuaba Bark, Horny Goat Weed |

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

While certain embodiments have been described above, various modifications to these embodiments will be readily apparent to those skilled in the art, and the generic principles described herein can be applied to other embodiments without departing from the spirit or scope of the invention. Thus, it is to be understood that the description presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method of vaporization delivery to a patient in need thereof consisting essentially of:
    extracting an herbal medicine containing cannabidiol from a *Cannabis* plant material, wherein the extraction step comprises the steps of: (1) adding the plant material to glycol to create a first composite; (2) storing the first composite at a temperature between about −34° C. to about −18° C. for at least about 4 hours; (3) grinding the first composite for about 5 to about 15 minutes to create a second composite; (4) storing the second composite at a temperature between about −34° C. to about −18° C. for at least about 4 hours; (5) grinding the second composite for about 5 to about 15 minutes to create a third composite; and (6) removing the unwanted material from the third composite to obtain said herbal medicine; and administering the herbal medicine in a carrier comprising a glycol wherein the herbal medicine is delivered to the patient through vaporization of the glycol.

2. The method of claim 1, wherein the first composite and second composite are stored at a temperature between about −34° C. to about −18° C. for about 8 hours.

3. The method of claim 1, wherein the first composite and second composite are ground for about 15 minutes.

4. The method of claim 1, wherein the first composite and second composite are stored at a temperature between about −34° C. to about −18° C. for about 8 hours and the first composite and second composite are ground for about 15 minutes.

5. The method of claim 1, wherein the glycol is propylene glycol.

6. The method of claim 1, wherein the carrier consists essentially of a glycol.

7. The method of claim 3, wherein the glycol is propylene glycol.

* * * * *